(12) United States Patent
Baholzer

(10) Patent No.: US 7,448,994 B2
(45) Date of Patent: Nov. 11, 2008

(54) ENDOSCOPE

(76) Inventor: Horst Baholzer, Winzerstr. 2, Freiburg (DE) 79111

( * ) Notice: Subject to any disclaimer, the term of this patent is extended or adjusted under 35 U.S.C. 154(b) by 667 days.

(21) Appl. No.: 10/907,900

(22) Filed: Apr. 20, 2005

(65) Prior Publication Data

US 2005/0240079 A1   Oct. 27, 2005

(30) Foreign Application Priority Data

Apr. 21, 2004   (DE) ........................ 10 2004 019 909

(51) Int. Cl.
*A61B 1/002* (2006.01)
*G02B 23/24* (2006.01)

(52) U.S. Cl. ........................ 600/138; 600/130; 359/434; 359/435

(58) Field of Classification Search ................. 600/138, 600/139, 101; 359/434, 435
See application file for complete search history.

(56) References Cited

U.S. PATENT DOCUMENTS

| | | | | |
|---|---|---|---|---|
| 1,915,811 A | * | 6/1933 | Wolf | 600/139 |
| 2,828,669 A | | 4/1958 | Peckham | 88/57 |
| 3,382,022 A | * | 5/1968 | Fox | 359/435 |
| 4,148,551 A | * | 4/1979 | MacAnally | 359/435 |
| 4,723,843 A | * | 2/1988 | Zobel | 359/435 |
| 5,020,893 A | * | 6/1991 | Karst et al. | 359/435 |
| 5,805,345 A | * | 9/1998 | Nagaoka | 359/654 |
| 5,841,578 A | * | 11/1998 | Hoogland | 359/434 |
| 5,888,193 A | * | 3/1999 | Breidenthal et al. | 600/160 |
| 5,900,971 A | * | 5/1999 | Ning | 359/435 |
| 6,201,649 B1 | * | 3/2001 | Rudischhauser et al. | 359/808 |
| 6,346,076 B1 | | 2/2002 | Rovegno | 600/173 |
| 6,398,723 B1 | | 6/2002 | Kehr et al. | 600/160 |
| 7,002,741 B2 | * | 2/2006 | Lei | 359/435 |
| 2002/0013570 A1 | | 1/2002 | Ruegg et al. | 606/1 |

FOREIGN PATENT DOCUMENTS

| | | |
|---|---|---|
| DE | 33 42 498 | 5/1984 |
| DE | 44 38 511 | 6/1995 |
| DE | 203 06 541 | 7/2003 |

\* cited by examiner

*Primary Examiner*—John P Leubecker
(74) *Attorney, Agent, or Firm*—Gudrun E. Huckett

(57) ABSTRACT

An endoscope has an endoscope tube and a lens system arranged in the endoscope tube. The lens system has endoscope lens components and air gaps between the lens components. An illumination system is arranged within the endoscope tube. The endoscope lens components each have an axial lens length; the endoscope lens components include first lens components and second lens components, wherein the axial lens length of the first lens components is the shortest axial lens length, respectively, and wherein the axial lens length of the second lens components is longer than the shortest axial lens length. The first lens components with the shortest axial lens length are arranged in an area of an axial center of the endoscope tube. The second lens components having the longer axial lens length have a first half and a second half and an air gap arranged between the first and second halves.

16 Claims, 3 Drawing Sheets

ENDOSCOPE

BACKGROUND OF THE INVENTION

The invention relates to an endoscope comprising an endoscope tube and a lens system with several lens components and air gaps arranged between the lens components as well as a light source, all parts being arranged within the endoscope tube. At least individual lens components have different axial lens lengths relative to one another and the shortest lens components are arranged in the area of the axial center of the endoscope tube.

Such an endoscope is disclosed in German patent document 203 06 541 U1. The endoscope can be bent greatly without damaging it because the shorter lens components are arranged in the area of the axial center of the endoscope tube. However, the bending characteristics of the endoscope are to be improved further.

Another endoscope is disclosed in German patent document 199 42 152. In this endoscope, between the objective and the ocular an optical image transmission system comprising several achromatic lenses is arranged. All lenses are identical. Disadvantageously, the endoscope tube can be bent only insufficiently during use in an operation or surgery.

U.S. Pat. No. 2,828,669 also discloses an endoscope wherein between the ocular and the objective doublets are arranged. All eight doublets are identical and the spacings between the individual doublets are also almost identical.

German patent 33 42 498 discloses an endoscope which is comprised of a plurality of lens assemblies wherein the lens assemblies are comprised of two lens members. The individual lens members have different lengths. Between the individual lens members there are no air gaps but between the lens members a glass plate is arranged so that flexing of the endoscope tube is prevented.

In another known endoscope, the lens system is comprised of several rod lenses having essentially identical length. When using the endoscope during an operation or surgery, for example, in the knee area, or for a urinary tract examination, bending of the endoscope tube occurs frequently. In the known endoscope, the endoscope tube can be deflected at its distal end (end distal to the operator) by approximately 20 mm. When bending is greater than this range, this disadvantageously leads to damage of the endoscope, in particular, breakage of the rod lenses can result.

Moreover, endoscopes are known in which the lens system has several sequentially arranged triplet systems. A triplet system is comprised of a long rod lens, a short lens, and another long rod lens.

SUMMARY OF THE INVENTION

It is an object of the present invention to further develop an endoscope of the aforementioned kind such that damage of the endoscope can be prevented even when greatly bending the endoscope.

As a solution to this object it is proposed according to the invention that the longer lens components are comprised of a first half and a second half, respectively, between which an air gap is arranged.

By arranging the shorter lens components of the endoscope lens components in the area of the axial center of the endoscope tube, the endoscope tube can be bent to a greater degree without the lens components becoming damaged. With the endoscope according to the invention, a deflection of the endoscope tube at the distal end of approximately 55 mm is possible. This is achieved in that in the area of greatest bending at the center of the endoscope tube a reduced bending resistance is present as a result of the shorter lens components. In order to obtain even more improved bending characteristics, the longer lens components of the endoscope lens components are comprised of a first half and a second half and between the first and second halves an air gap is arranged. In this way, when bending occurs, the risk of breakage of the rod lens is reduced because it is more flexible as a whole as a result of an air gap being provided between the two halves.

In addition, the contact length of the lens component with the interior tube and thus the breakage risk of the rod lens upon bending is reduced further in one embodiment in that the outer diameter of the longer lens component is reduced in a partial area of the lens component and, in particular, the outer diameter of the two halves of the longer lens component is reduced in a partial area of each half, respectively.

When using the endoscope, the greatest bending action occurs at the center of the endoscope tube and a reduced bending action occurs in the direction toward the ends of the endoscope tube; therefore, a preferred embodiment of the invention provides that the lengths of the lens components increase from the area of the axial center of the endoscope tube at least toward one end of the endoscope tube. Advantageously, the lengths of the lens components increase from the area of the axial center to the distal end (end remote from the operator) and also to the proximal end (end facing the operator) of the endoscope tube.

The ratio of the axial lens lengths of the individual endoscope lens components relative to one another can be rather different. It was found to be expedient to select the ratio of axial lens lengths of the longest lens components to the axial lens length of the shortest lens component to be approximately 7:1. Furthermore, it was found to be expedient to select the axial gap length of the air gap adjoining the shortest lens component to be approximately identical to or a multiple of, in particular five times, the shortest axial lens length of the shortest lens component.

The bendability of the endoscope tube can be increased additionally when instead of the customarily employed stainless steel endoscope tubes an endoscope tube of a somewhat more flexible material is employed. A further preferred embodiment of the invention therefore provides that the exterior tube of the endoscope tube is comprised of a flexible metal alloy.

DESCRIPTION OF THE PREFERRED EMBODIMENTS

Figure 1:
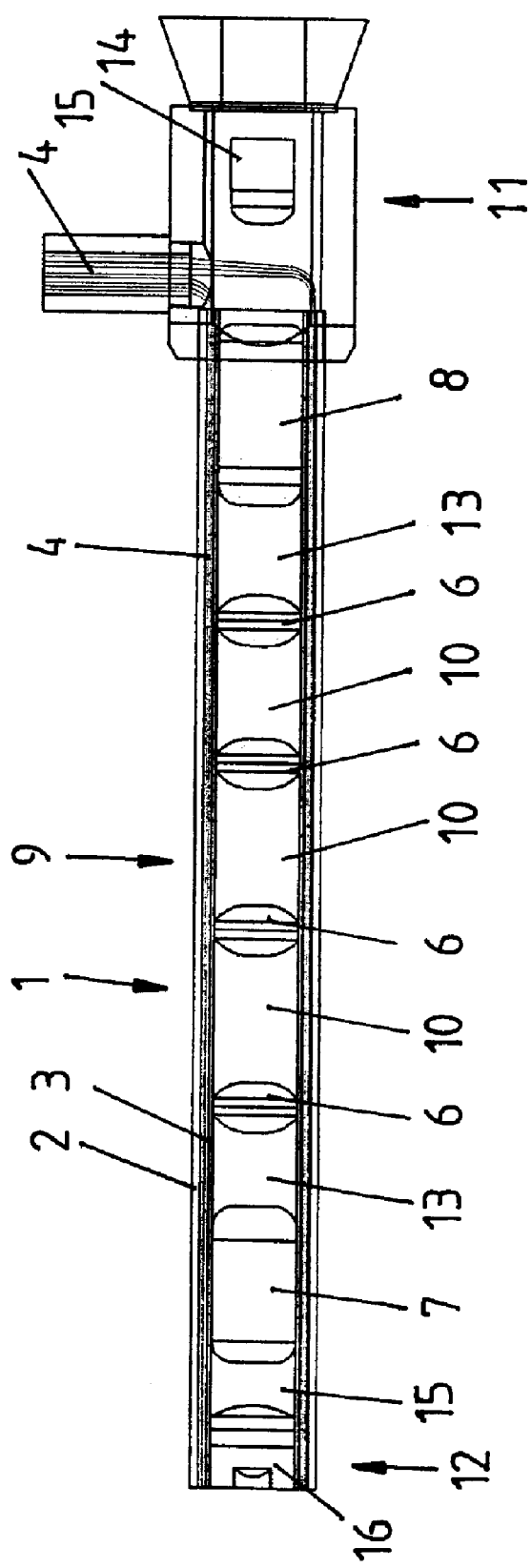
FIG. 1 is a longitudinal section of the endoscope according to the invention according to a first embodiment.

The endoscope according to the invention has an endoscope tube 1 comprising an exterior tube 2 and an interior tube 3 arranged within the exterior tube 2. Between the exterior tube 2 and the interior tube 3, there are a plurality of light guides as an illumination device 4. Within the interior tube 3 a lens system 5 is arranged that is comprised of a total of six endoscope lens components 6, 7, 8 in accordance with FIG. 1 or ten endoscope lens components 6, 7, 8 in accordance with FIG. 2. The individual endoscope lens components 6, 7, 8 have different axial lens lengths. There are four first lens components 6 according to FIG. 1 arranged in the area of the axial center 9 of the endoscope tube 1 that have the shortest axial lens length (approximately 4 mm, respectively) of the endoscope lens components. The four first lens components 6 are separated from one another by a total of three air gaps 10. The axial gap length of each air gap 10 is 20 mm and is thus approximately 5 times the axial lens length of 4 mm of the shortest lens components 6. Adjacent to the exterior lens components 6 an additional air gap 13 is provided, respectively, in the direction toward the proximal end 11 as well as the distal end 12 of the endoscope tube 1; this air gap 13 is somewhat shorter than the air gap 10. In the direction toward the distal end 12 a longer second lens component 7 having an axial lens length of 23 mm adjoins the air gap 13; in the direction toward the distal end 11 an even longer second lens component 8 having an axial lens length of 28 mm adjoins the air gap 13. In the direction toward the proximal end 11, another air gap and an ocular 14 are provided. In the direction toward the distal end 12, an air gap 15 and an objective 16 are provided downstream of the lens component 7.

Figure 2:
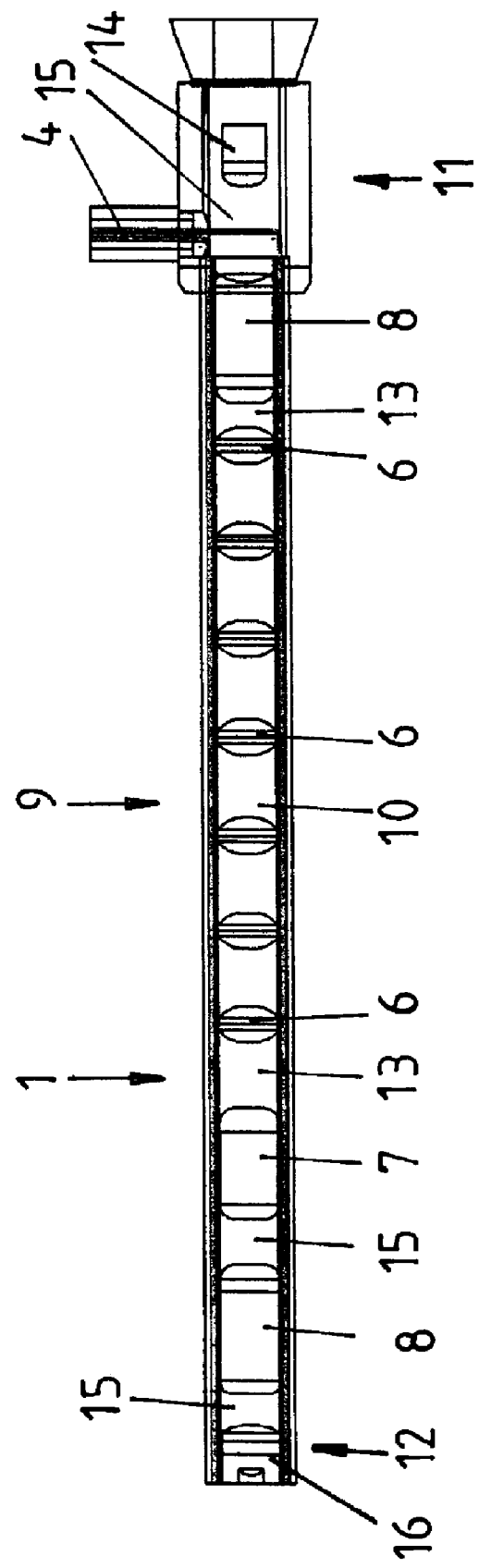
FIG. 2 is a longitudinal section of the endoscope according to the present invention according to a second embodiment.

In the embodiment according to FIG. 2, in the area of the axial center 9 of the endoscope tube 1, there are a total of seven short lens components 6 having the shortest axial lens length of 4 mm, respectively. The air gaps 10 therebetween again have an axial gap length of 20 mm. In the direction toward the proximal end 11 as well as toward the distal end 12 of the endoscope tube 1, a further air gap 13 adjoins the outer lens component 6, respectively; the air gap 13 can be somewhat shorter than the air gap 10. Adjoining the air gap 13 in the direction toward the distal end 12, sequentially a longer lens component 7 having an axial lens length of 23 mm, another air gap 15, and an even longer lens component 8 having a length of 27 mm are provided. Toward the proximal end 11 downstream of the air gap 13 the longer lens component 8 having a length of 27 mm is provided. Downstream thereof, an air gap 15 and the ocular 14 are arranged. In the direction toward the distal end 12, an air gap 15 and the objective 16 are provided downstream of the lens component 8.

The longer lens components 7 and lens components 8 illustrated in FIGS. 1 and 2 are rod lenses and are of a monolithic configuration and have a length of approximately 21 mm to 30 mm and an outer diameter of approximately 1.8 mm to 2.8 mm.

Figure 3:
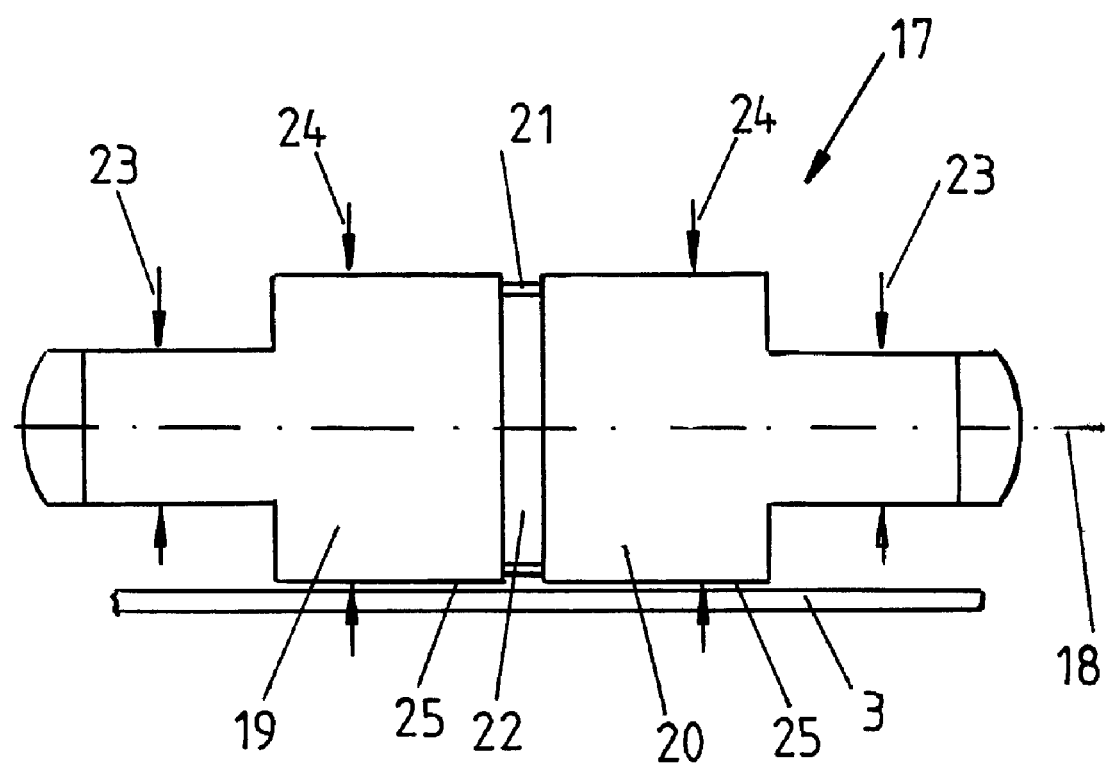
FIG. 3 is a longitudinal section of a longer lens component.

FIG. 3 shows a further configuration of a longer lens component 17. With regard to its axial lens length, this lens component 17 matches the lens component 7 or 8, but the lens component 17 is centrally divided in half perpendicularly to its longitudinal axis 18 so that a first half 19 and a second half 20 of the lens component 17 are formed. Between the first half 19 and the second half 20, spacer elements 21 are arranged such that between the two halves 19, 20 an air gap 22 of 1 mm axial gap length is formed. The outwardly facing free end of each of the halves 19, 20 is ground relative to its center such that the outer diameter 23 of a partial area of the outer free end of each half 19, 20 is smaller than an outer diameter 24 of the remaining area of each half 19, 20 of the lens component 17. For an outer diameter 24 of 1.8 mm, the outer diameter 23 is 1.4 mm and for an outer diameter 24 of 2.8 mm the outer diameter 23 is 2.2 mm. The reduced outer diameter 23 extends from the free end of the first half 19 in the axial direction of the longitudinal axis 18 approximately to the center of the total length of the first half 19. Correspondingly, in the case of the second half 20 the reduced outer diameter 23 in the axial direction of the longitudinal axis 18 extends to the center of the second half 20. By dividing in half the longer lens component 17 and providing the reduced outer diameter 23, improved bending characteristics of the endoscope according to the invention result because the contact length 25 of the lens component 17 that rests against the inner wall of the interior tube 3 is significantly shorter than the corresponding contact length of the lens components 7 and 8. Accordingly, upon bending the interior tube 3 the risk of breakage of the lens component 17 is significantly reduced. For the afore described lens component 17 according to FIG. 3 the contact length 25 is only half as great as a contact length of the corresponding monolithic lens component 7 or 8. The uniformly reduced outer diameter 23 of the two halves 19, 20 could be located alternatively at the inner ends of the two halves 19, 20 that are arranged so as to face one another adjacent to the air gap 22.

By arranging the shortest lens components 6 in the area of the center 9 of the endoscope tube 1, a great bending of the endoscope tube 1 when using the endoscope according to the invention is possible without the lens components 6, 7, 8 becoming damaged by the bending action. In addition, this greater bendability of the endoscope tube 1 is improved further by the relatively great air gap 10 in comparison to the length of the lens components 6. An even greater bendability of the endoscope tube 1 is achieved in that the exterior tube 2 is comprised of a flexible metal alloy. As a metal alloy, a nickel-cobalt-chromium alloy, in particular, Phynox®, is used. The lens system 5 can have an outer diameter of 1.8 mm or 2.8 mm. In accordance therewith, the outer diameter of the exterior tube 2 is 2.7 mm or 4 mm. By dividing in half the longer lens component 17 and reducing the outer diameter 23 of the two halves 19, 20, an even more improved bending action of the endoscope according to the invention results.

While specific embodiments of the invention have been shown and described in detail to illustrate the inventive principles, it will be understood that the invention may be embodied otherwise without departing from such principles.

What is claimed is:

1. An endoscope comprising:
   an endoscope tube;
   a lens system arranged in the endoscope tube and comprising lens components and first air gaps between the lens components;
   an illumination system arranged within the endoscope tube;
   wherein the endoscope lens components each have an axial lens length;
   wherein the endoscope lens components comprise first lens components and second lens components, wherein the axial lens length of the first lens components is the shortest axial lens length, respectively, and wherein the axial lens length of the second lens components is longer than the shortest axial lens length;
   wherein the first lens components with the shortest axial lens length are arranged in an area of an axial center of the endoscope tube;
   wherein the second lens components having the longer axial lens length are comprised of a first half and a second half and a second air gap arranged between the first and second halves;
   wherein the second lens components have a partial area having a reduced outer diameter, respectively.

2. The endoscope according to claim 1, wherein the axial lens length of the endoscope lens components increases from the axial center of the endoscope tube at least toward one end of the endoscope tube.

3. The endoscope according to claim 1, wherein the axial lens lengths of the endoscope lens components increase from the axial center of the endoscope tube toward a proximal end and toward a distal end of the endoscope tube.

4. The endoscope according to claim 1, wherein the ratio of the axial lens length of a longest one of the endoscope lens components to the shortest axial lens length of the first lens components is approximately 7:1.

5. The endoscope according to claim 1, wherein the axial lens lengths of the endoscope lens components decease continuously from a proximal end of the endoscope to the axial center and increase continuously from the center to a distal end of the endoscope.

6. The endoscope according to claim 1, wherein in the area of the axial center several of the first lens components are arranged.

7. The endoscope according to claim 6, wherein four of the first lens components are provided.

8. The endoscope according to claim 6, wherein seven of the first lens components are provided.

9. The endoscope according to claim 8, wherein seven of the first lens components are provided and six of the first air gaps are provided.

10. The endoscope according to claim 6, wherein between the first lens components several of the first air gaps are provided, wherein the first air gaps each have an axial gap length that is a multiple of the shortest axial lens length.

11. The endoscope according to claim 10, wherein four of the first lens components are provided and three of the first air gaps are provided.

12. The endoscope according to claim 1, wherein the endoscope tube comprises an exterior tube and an interior tube wherein the exterior tube is made of a flexible metal alloy.

13. An endoscope comprising:

an endoscope tube;

a lens system arranged in the endoscope tube and comprising lens components and first air gaps between the lens components;

an illumination system arranged within the endoscope tube;

wherein the endoscope lens components each have an axial lens length;

wherein the endoscope lens components comprise first lens components and second lens components, wherein the axial lens length of the first lens components is the shortest axial lens length, respectively, and wherein the axial lens length of the second lens components is longer than the shortest axial lens length;

wherein the first lens components with the shortest axial lens length are arranged in an area of an axial center of the endoscope tube;

wherein the second lens components having the longer axial lens length are comprised of a first half and a second half and a second air gap arranged between the first and second halves;

wherein the first and second halves each have a partial area having a reduced outer diameter.

14. An endoscope comprising:

an endoscope tube;

a lens system arranged in the endoscope tube and comprising lens components and first air gaps between the lens components;

an illumination system arranged within the endoscope tube;

wherein the endoscope lens components each have an axial lens length;

wherein the endoscope lens components comprise first lens components and second lens components, wherein the axial lens length of the first lens components is the shortest axial lens length, respectively, and wherein the axial lens length of the second lens components is longer than the shortest axial lens length;

wherein the first lens components with the shortest axial lens length are arranged in an area of an axial center of the endoscope tube;

wherein the second lens components having the longer axial lens length are comprised of a first half and a second half and a second air gap arranged between the first and second halves;

wherein an axial gap length of one of the first air gaps adjoining one of the first lens components is identical to or a multiple of the shortest axial lens length.

15. The endoscope according to claim 14, wherein the second lens components have a partial area having a reduced outer diameter, respectively.

16. The endoscope according to claim 14, wherein the axial gap length of said first air gap is five times the shortest axial lens length.

* * * * *